United States Patent
Gorringe et al.

(10) Patent No.: US 7,820,185 B2
(45) Date of Patent: Oct. 26, 2010

(54) STABLE COMPOSITIONS CONTAINING OMVS

(75) Inventors: Andrew R. Gorringe, Salisbury (GB); Phillip Vincent, Salisbury (GB); Denise Halliwell, Salisbury (GB); Karen M. Reddin, Salisbury (GB)

(73) Assignee: Health Protection Agency, Salisbury, Wiltshire (GB)

( * ) Notice: Subject to any disclaimer, the term of this patent is extended or adjusted under 35 U.S.C. 154(b) by 596 days.

(21) Appl. No.: 11/632,794

(22) PCT Filed: Jul. 18, 2005

(86) PCT No.: PCT/GB2005/002817

§ 371 (c)(1), (2), (4) Date: Jan. 18, 2007

(87) PCT Pub. No.: WO2006/008504

PCT Pub. Date: Jan. 26, 2006

(65) Prior Publication Data

US 2009/0041807 A1  Feb. 12, 2009

(30) Foreign Application Priority Data

Jul. 19, 2004  (GB) ................................. 0416120.4

(51) Int. Cl.
*A61K 39/095* (2006.01)
(52) U.S. Cl. ................................. 424/249.1; 424/250.1
(58) Field of Classification Search ........................ None
See application file for complete search history.

(56) References Cited

U.S. PATENT DOCUMENTS

| 7,179,484 B2 * | 2/2007 | Singh .......................... 424/450 |
| 2003/0138453 A1 * | 7/2003 | O'Hagan et al. ......... 424/199.1 |

FOREIGN PATENT DOCUMENTS

| EP | 0 301 992 A3 | 2/1989 |
| EP | 0 624 376 A1 | 11/1994 |
| WO | WO 92/05194 A1 | 4/1992 |
| WO | WO 01/09350 A3 | 2/2001 |
| WO | WO 01/91788 A1 | 12/2001 |
| WO | WO 03/051379 A1 | 6/2003 |
| WO | WO 2004/019977 A3 | 3/2004 |

OTHER PUBLICATIONS

Haake, et al.; Characterization of the Leptospiral Outer Membrane and Description of Three Novel Leptospiral Membrane Proteins; Infection and Immunity, Sep. 2002, vol. 70, No. 9; pp. 4936-4945.
Arigita, et al.; Stability of Mono- and Trivalent Meningococcal Outer Membrane Vesicle Vaccines; Vaccine vol. 22, No. 5-6; Jan. 26, 2004; pp. 629-643. XP004485193.
Arigita, et al.; Restored Functional Immunogenicity of Purified Meningoccal PorA by Incorporation Into Liposomes; Vaccine vol. 21, No. 9-10; Feb. 14, 2003; pp. 950-960. XP004402623.
Van Der Ley, et al.; Construction of *Neisseria meningitidis* Strains Carrying Multiple Chromosomal Copies of the PorA Gene for Use in the Production of a Multivalent Outer Membrane Vesicle Vaccine; Vaccine 1995, vol. 13, No. 4; pp. 401-407. XP004057740.

\* cited by examiner

*Primary Examiner*—Robert Mondesi
*Assistant Examiner*—Khatol Shahnan-Shah
(74) *Attorney, Agent, or Firm*—Hodgson Russ LLP (57) ABSTRACT

An OMV preparation comprises OMVs having a sufficiently positive or negative surface charge to substantially prevent aggregation.

21 Claims, 6 Drawing Sheets

A: Particle size distribution of *N. lactamica* OMVs after thawing
Size Distribution by Intensity B: Particle size distribution of *N. lactamica* OMVs after filtration using Mini KleenPak EKV filters (Pore size 0.65/0.2 µm, Pall UK)
Size Distribution by Intensity

FIG. 3A

Results

| | | | |
|---|---|---|---|
| Z-Average size (nm): 185.7 | Peak 1 Mean: 168.6 | % (Intensity): 77 | Width: 66.7 |
| Polydispersity index: 0.445 | Peak 2 Mean: 222.9 | % (Intensity): 22 | Width: 328.9 |
| | Peak 3 Mean: 0 | % (Intensity): 0 | Width: 0 |

— Record 93: pH8 glycine + 9500rpm (pre filter)

FIG. 3B

Results

| | | | |
|---|---|---|---|
| Z-Average size (nm): 134 | Peak 1 Mean: 154.6 | % (Intensity): 100 | Width: 59.42 |
| Polydispersity index: 0.127 | Peak 2 Mean: 0 | % (Intensity): 0 | Width: 0 |
| | Peak 3 Mean: 0 | % (Intensity): 0 | Width: 0 |

— Record 102: pH8 glycine + 9500rpm (0.8/0.2 post filter)

FIG. 3C

Results

| | | | |
|---|---|---|---|
| Z-Average size (nm): 129.3 | Peak 1 Mean: 158 | % (Intensity): 100 | Width: 73.62 |
| Polydispersity index: 0.177 | Peak 2 Mean: 0 | % (Intensity): 0 | Width: 0 |
| | Peak 3 Mean: 0 | % (Intensity): 0 | Width: 0 |

—— Record 123: 4ml/min pH8 gly 30-12-03

FIG. 4

MFA717cp.tif
N.lactamica OMVs sample 3,
made June 05, PBS - EM no. 29/05
Print Mag: 64800x @ 7.0 in
11:58 06/15/05

500 nm
Direct Mag: 39000x

FIG. 5

MFA718c.tif
N.lactamica OMVs sample 4,
made June 05, glycine buffer - EM no. 30/05
Print Mag: 64800x @ 7.0 in
17:10 06/15/05

500 nm
Direct Mag: 39000x

STABLE COMPOSITIONS CONTAINING OMVS

The present invention relates to compositions comprising vesicles, sterile compositions comprising vesicles and in particular such compositions comprising outer membrane vesicles (OMVs) of bacteria for use in vaccination, together with methods of preparing such compositions.

A number of vaccines are known or are in development which contain bacterial outer membrane vesicles. These vaccines are preferably prepared under aseptic conditions, more preferably sterile conditions.

*Neisseria meningitidis* outer membrane vesicle (OMV) vaccines have been used in clinical studies for the prevention of meningococcal disease. Vaccines produced in Norway (Fredriksen et al. 1991), Cuba (Sierra et al. 1991) and the Netherlands (Claassen et al. 1996) have used the preservative thiomersal to ensure the sterility of these vaccines. However, it is now considered a disadvantage to rely on the presence of a preservative.

Known methods of sterilisation of pharmaceutical compositions include heat-treatment and the use of radiation. Whilst these methods are suitable for sterilising many compositions, they are not suitable for sterilising compositions comprising outer membrane vesicles, as these vesicles are damaged both by heat and radiation.

Preparations of OMVs typically comprise OMVs of a wide range of sizes, from 0.01 microns to 1 micron in diameter. In addition, OMVs have a tendency to aggregate and this commonly results in preparations of OMVs having approximately biphasic patterns of size distribution, with a large number of particles having a mean diameter of approximately 0.1 micron and another set having a mean diameter of approximately 2 microns.

Another known method of sterilisation is to use a sterile filter having a pore size of approximately 0.2 microns in diameter. This method is effective in sterilising known OMV preparations, but has the significant disadvantage that a large proportion of such preparations consists of OMVs/aggregates which, prior to filtration, are larger in diameter than the filter pore size. Hence, while a sterile composition is obtained there is a loss of product of approximately 70% or worse. This loss of product is unacceptable in a process which is scaled-up for vaccine manufacture. The process of filtration also tends to increase the coalescence of OMVs, leading to increased loss of product during filtration.

Good manufacturing practice for vaccines requires a sterile product. Hence, it is an object of the present invention to provide an improved method for sterilisation of compositions comprising vesicles, together with the composition thereby obtained. A further object of specific embodiments of the invention is to provide a stabilised vesicle-containing formulation and, in further specific embodiments, to provide control of coalescence of vesicles.

Accordingly, the present invention provides OMV preparations, methods of obtaining them, and uses thereof, in which the OMVs are stable and/or non-aggregating and can be sterilised, for example by passing the OMVs through a filter as mentioned above.

Methods of the invention comprise treating OMVs to alter their surface charge so as to reduce aggregation. A first such method comprises suspending OMVs in a solution which imparts a surface charge to the OMVs that is sufficiently high to prevent aggregation.

Of course, sufficiently high refers to the magnitude of the surface charge of the OMVs, and could be a sufficiently high positive charge or could be a sufficiently high negative charge. These possibilities are discussed further below.

Solutions that are capable of imparting a high surface charge to the OMVs are suitably buffer solutions, and can include hydrochloric acid/potassium chloride, glycine/hydrochloric acid, potassium hydrogen phthalate/hydrochloric acid, citric acid/sodium citrate, sodium acetate/acetic acid, potassium hydrogen phthalate/sodium hydroxide, disodium hydrogen phthalate/sodium dihydrogen orthophosphate, dipotassium hydrogen phthalate/potassium dihydrogen orthophosphate, barbitone sodium/hydrochloric acid, tris (hydroxymethyl)aminomethane/hydrochloric acid, sodium tetraborate/hydrochloric acid, glycine/sodium hydroxide, sodium carbonate/sodium hydrogen carbonate, sodium tetraborate/sodium hydroxide, sodium hydrogen orthophosphate/sodium hydroxide, potassium chloride/sodium hydroxide. Most preferred buffers include those containing borate, carbonate, bicarbonate, glycine or tris (hydroxymethyl)aminomethane, such as those buffers mentioned above that contain these components.

Particular embodiments, giving good results, can comprise glycine-containing buffers, although any buffer solution that increases the magnitude of the surface charge of the vesicles is suitable for use in the invention. In a preferred embodiment, the buffer solution is a 0.2M or greater glycine buffer (preferably 0.2M to 0.5M glycine, more preferably, 0.2M to 0.3 M glycine, most preferably about 0.2M glycine), at pH 8 or higher (preferably, pH 8 to pH 9, more preferably pH 8 to pH 8.5, most preferably about pH 8), optionally supplemented by a sugar at 1% or more by weight (e.g., 1% to 3% by weight, most preferably about 1% by weight), preferably sucrose. Alternatively, solutions capable of imparting a high surface charge to the OMVs can comprise solutions having a pH equal to or greater than 8, preferably equal to or greater than 8.5, more preferably equal to or greater than 9. Thus preferred pH ranges for buffering the compositions of the invention include, pH 7.5 to pH 9, more preferably pH 8 to pH 8.5, most preferably about pH 8.

The inventors have found that by raising the magnitude of the surface charge of a given OMV preparation, the aggregation of the vesicles is reduced. Surface charge of particles in suspension is conveniently measured by instruments widely available and can be reported as zeta potential. Zeta potential can be measured, for example, using a Zetasizer (Malvern Instruments, Malvern Instruments Ltd, Enigma Business Park, Grovewood Road, Malvern, Worcestershire, UK, WR14 1XZ) and can give an indication of how likely the OMVs are to aggregate; typically, if the zeta potential is within the range −15 to 15 mV, the OMVs are more likely to aggregate. In the examples disclosed herein, it has been found that when the zeta potential of an OMV preparation is relatively close to zero, the OMVs are highly aggregated (aggregation assessed by Differential Interference Contrast (DIC) Microscopy, see Table 1).

When the buffering conditions of the OMV preparations are altered so that the zeta potential of the preparation is moved away from zero (i.e. made either more negative or more positive, preferably to fall outside the range −15 to 15 mV, more preferably outside the range −30 mV to 30 mV, most preferably outside the range −40 to 40 mV) the OMVs are found to be substantially less aggregated and thus more stable (see Table 1).

Stable OMV preparations have several other important advantages. In particular, they are easier to process, e.g. filter, than preparations in which the OMVs are in an aggregated state. This allows sterile preparations to be produced (e.g., by filter sterilisation) that can then be stored in the absence of a preservative such as thiomersal. Thus in a preferred embodiment of the invention, the preparations are preservative free, e.g., thiomersal free. The invention also allows the OMVs to be stored frozen (−20 to −80 C, such as at −20 C or −70 C, most preferably −20 C) and thawed without creating an aggregated product. Further, methods for generating stable OMV preparations are useful in reducing the batch-to-batch variation in particle size that can occur in large scale manufacture of OMV preparations, e.g. in the manufacture of OMV vaccines. An evenly distributed suspension of OMVs allows more reproducible and consistent vaccines to be produced, such as those with a more consistent ability to raise antibodies in mice.

The term "stable" as used in this specification refers to preparations of the invention wherein the OMVs are substantially non-aggregating. In one embodiment of the invention, a preparation of OMVs that is non-aggregating is one in which a high proportion of the OMVs have not formed aggregates with other OMVs. Preferably not more than 60% of the OMVs have formed aggregates with other OMVs, more preferably not more than 40%, most preferably not more than 30% (as measured by particle size analysis e.g. using a Zetasizer, Malvern Instruments).

It has been found that for OMVs suspended in alkaline buffer, the particle size distribution (measured using a Zetasizer) remains substantially unchanged over a 24 hour period (see Table 2). Thus, in a further embodiment of the invention, a preparation of OMVs that is non-aggregating is one in which the mean particle size of the preparation does not increase over a 24 hour period by more than 20%, preferably by no more than 10%.

Preparations of OMVs are also considered non-aggregating if the mean diameter of the particles in the preparation is less than 250 nm, 200 nm, preferably less than 180 nm, more preferably less than 160 nm, measured, for example, using the apparatus described above.

Non-aggregating preparations of OMVs can also be defined by the percentage of OMVs that is recovered following filtration through a membrane (as measured by % post-filtration protein recovery). For example, preparations of OMVs may be considered non-aggregating if, after passage through a filter having a pore size in the range 0.2-1 microns, in particular through a filter having an average pore diameter of 0.2 µm, a protein recovery of at least 70% is achieved, preferably at least 75%. Preparations allowing at least 70-90% protein recovery, preferably up to 97%, after passage through a filter having a pore size in the range 0.2-0.45 microns, are also considered non-aggregating. When passed through two filters, the first filter having a pore size in the range 0.5-1 microns and the second in the range 0.2-0.5 microns, a preparation will be non-aggregating if a final protein recovery of at least 70% is achieved, preferably at least 80%.

Prevention of aggregation can therefore be defined further by any of the above definitions. Particularly preferred preparations are stable according to all of the above definitions.

The invention applies in particular to OMVs from Gram negative bacteria, being those bacteria that fail to resist decolourisation in the commonly known Gram staining method. Gram negative bacteria are characterised by a complex multilayer cell wall and often possess an outer layer polysaccharide capsule—e.g. *N. meningitidis*, although in some species this capsule is absent—e.g. *N. lactamica*. In general, all such bacteria are believed suitable, though Gram negative species especially suitable for use in the invention include those selected from *Neisseria, Moraxella, Kingella, Acinetobacter, Brucella, Bordetella, Porphyromonas, Actinobacillus, Borelia, Serratia, Campylobacter, Helicobacter, Haemophilus, Escherichia, Legionella, Salmonella, Pseudomonas* and *Yersinia*. In a particular embodiment of the invention the composition comprises OMVs from strains of *Neisseria*. Preferred *Neisseria* include *Neisseria meningitidis* and *Neisseria gonorrhoeae*.

The invention also applies to commensal organisms, i.e. those that coexist in an environment with another organism, such coexistence being beneficial to at least one of the organisms and generally not detrimental to either. A number of different commensal *Neisseria* are suitable for use in the invention, and these commensal *Neisseria* may be selected from the group consisting of *N. lactamica, N. cinerea, N. elongata, N. flavescens, N. polysaccharea, N. sicca* and *N. subflava*.

The invention may be applied to both OMVs derived from genetically-modified bacteria and to OMVs prepared from non-genetically modified (naturally occurring or wild-type) *Neisseria*.

A known OMV vaccine is composed of OMVs from bacteria that have been genetically modified to express more than one PorA (Class 1) antigen in their membranes (Claassen et al., 1996). In addition, Class 3 protein (now known as PorB) is deleted and PorA makes up approximately 90% of the total protein in the OMV (Claassen et al., 1996). These modifications are capable of imparting to the OMVs a high surface charge, and yet the OMVs nevertheless form aggregates in solution, as reported in the art (Arigita et al., Vaccine 22 (2004), page 629-642).

Methods of the invention are distinct from and do not include known preparations of these known genetically-modified OMVs. Hence, the invention also provides a method of stabilising an OMV preparation, comprising suspending OMVs in a solution having a zeta potential outside the range −15 mV to 15 mV, wherein the OMVs are not genetically modified so as to delete PorB and/or express more than one PorA protein. As noted above, the OMV preparations of the invention exclude those disclosed in Arigita et al (that is, preparations which are genetically modified to have PorB deleted and preparations which are genetically modified to have PorB deleted and more than one PorA expressed).

However, it is possible, if desired, to carry out the method of the present invention on OMVs genetically-modified to delete PorB and/or express more than one PorA. This is achieved by further increasing the magnitude of the zeta potential of the genetically-modified OMV preparation by at least 10 mV, preferably by at least 20 mV. Thus, in the case of OMVs of the type described in Arigita et al., where the zeta potentials of the preparations are −42 mV, −48 mV and −49 mV, these zeta potentials would be increased to at least −52, −58 mV and −59 mV respectively.

Thus, in accordance with the invention, the magnitude of the zeta potential may be increased by about 10 mV, for example, may be made about 10 mV more negative than the starting value, more preferably the zeta potential may be made more negative by about −20 mV, even more preferably by −30 mV. Thus the change in magnitude of the zeta potential may be −5 mV to −30 mV, more preferably −10 mV to −20 mV, even more preferably −5 mV to −15 mV, more preferably −8 mV to −12 mV, most preferably about −10 mV.

The magnitude of the zeta potential may be made about 10 mV more positive than the starting value, more preferably the zeta potential may be made more positive by about +20 mV, even more preferably by +30 mV. Thus the change in magnitude of the zeta potential may be +5 mV to ∓30 mV, more preferably +10 mV to +20 mV, even more preferably +5 mV to +15 mV, more preferably +8 mV to +12 mV, most preferably about +10 mV.

The surface charge imparted according to the invention has the advantage that the OMVs are readily redispersed, and hence a method of the invention comprises suspending the OMVs in a solution having a zeta potential outside the range −15 mV to 15 mV, and homogenising the resultant suspension. Preferably the zeta potential of the solution is outside the range −30 mV to 30 mV, more preferably outside the range −40 to 40 mV. The homogenisation can be carried out as either a one or two-step process, although preferably it is a two-step process. Any suitable homogeniser can be used (for example those available from Silverson Machines Ltd., Waterside, Chesham, Bucks, HP51 PQ). In a particular embodiment of the two-step homogenisation process, the OMV preparation is homogenised at a speed of at least 800 rpm for at least 5 minutes, and subsequently at a speed of at least 9500 rpm for at least 5 minutes. Suitably, the homogenisation is carried out in a Ultra-turrax T25 homogeniser.

The OMVs homogenised are preferably not those from the known vaccine, and hence it is preferred that the OMVs are not genetically modified so as to delete PorB and/or express more than one PorA protein.

The homogenisation of the OMV preparations results in disperse preparations that remain stable over a substantial period of time, preferably for at least 24 hours, e.g., at 4° C. The maintenance of this stability in specific embodiments of the invention is demonstrated in Table 2.

A further aspect of the invention provides a method of stabilising an OMV preparation comprising:
(i) obtaining a preparation of OMVs in a solution, and
(ii) adjusting the zeta potential of the solution to fall outside the range −15 mV to 15 mV. Preferably, the zeta potential is adjusted to be outside the range −30 to 30 mV, more preferably outside the range −40 to 40 mV.

Again, the OMVs are preferably not those from the known vaccine, and are therefore preferably not genetically modified so as to delete PorB and/or express more than one PorA protein. For OMVs having a naturally high surface charge, but which nevertheless aggregate unacceptably, the invention can be carried out by further increasing the zeta potential of the solution.

There are several ways in which the zeta potential of the solution can be adjusted in order to stabilise the OMV preparation. In certain embodiments, this is achieved by altering the pH of the solution, preferably so that the pH of the solution is equal to or less than pH 6, or equal to or greater than pH 8, preferably equal to or greater than pH 8.5 or equal to or greater than pH 9. In other embodiments, the zeta potential is adjusted by altering the ionic strength of the solution, for example by the addition of ions (e.g., $Ca^{2+}$, $Mg^{2+}$, $Na^+$, $Cl^-$ or $NH_4^+$) to the solution, or by altering the temperature of the solution, for example by lowering the temperature of the solution. The skilled person can measure the effect on the zeta potential of the OMV preparation using known techniques, such as those disclosed in this application.

For certain OMV preparations, adjustment of the pH adjusts the zeta potential and/or surface charge so as to reduce aggregation, and the invention provides a further method of stabilising an OMV preparation, comprising suspending the OMVs in a solution having a pH equal to or greater than 8, preferably a pH equal to or greater than 8.5.

Prior to using or processing OMVs, it is desired to ensure they are non-aggregated. Following the invention this can be achieved in a method of preventing aggregation of OMVs comprising (i) obtaining a preparation of OMVs in a solution,
(ii) measuring the aggregation of the OMVs in said solution,
(iii) if the OMVs are aggregated, adjusting the zeta potential of the solution, and returning to step (ii). The method can further comprise a homogenisation step after step (iii). In certain embodiments, the preparation obtained after step (iii), or after homogenisation, is subsequently frozen for storage. The inventors have found that when these frozen preparations are thawed, the stability of the OMV preparation is maintained. This provides a significant advantage over known OMV preparations, where the thawed preparations are found to be largely aggregated. This the present invention provides OMVs that are stable when frozen at −20 C for about 24 hours, more preferably at least 1 week, more preferably at least one month, more preferably at least, or about, six months, more preferably at least, or about 10 months, more preferably at least, or about, one year.

In step (i) of the above method, the aggregation of the OMVs can be measured by Differential Interference Contrast (DIC) microscopy or by particle size analysis (e.g. using a Zetasizer), and in certain instances, the OMV preparations can be considered to be aggregated when the mean particle diameter is in excess of 200 nm. The adjustment of the zeta potential in the above method can be carried out as described in previous embodiments of the invention, for example by altering the pH, ionic strength and/or temperature of the solution.

The filtration of OMVs is an important step in the production of many OMV-containing compositions, especially vaccines. It is therefore desirable to be able to filter OMV preparations efficiently, i.e. with low loss of OMVs in the filtration process.

Aggregates of OMVs do not pass easily, and in some cases not at all, through filters with specified pore sizes. The invention solves this problem in a method of filtering an OMV preparation, comprising:—

(i) suspending OMVs in a solution which imparts a surface charge to the OMVs that is sufficiently high to prevent aggregation, and (ii) filtering the resultant suspension through a filter membrane.

An alternative method of filtering an OMV preparation comprises:—

(i) suspending the OMVs in a solution having a zeta potential falling outside the range −15 mV to 15 mV, and (ii) filtering the resultant suspension through a filter membrane.

A still further method of filtering an OMV preparation comprises:—

(i) stabilising an OMV preparation according to any method of the invention, and (ii) filtering the resultant stabilised preparation through a filter membrane.

These filtration methods may further comprise a homogenisation step between steps (i) and (ii).

In the above methods, preferably at least 60% (more preferably at least 70%, more preferably at least 80%, more preferably at least 90%) of the OMVs in step (i) have a mean diameter of less than 250 nm, less than 200 nm, less than 180 nm or less than 160 nm; more preferably at least 70% have a mean diameter of less than 170 nm. The filter membrane of step (ii) in these methods preferably has a pore size of from 0.2-2 microns (e.g., filters having an average pore diameter of 0.2 μm).

In these methods, preferably at least 70% (more preferably at least 80%, more preferably at least 90%) of the OMVs in step (ii) have a mean diameter of less than 200 nm, less than 180 nm or less than 160 nm; more preferably at least 70% have a mean diameter of less than 170 nm, more preferably less than 160 nm, most preferably less than 150 nm.

It is also known to use filtration as a means of sterilising OMV preparations. However, filtration of OMVs through Minisart™ 0.2 µm syringe filters (Sartorius Ltd., Longmead Business Park, Blenheim Road, Epsom, Surrey, KT19 9QQ, UK), routinely used in the laboratory for filter sterilisation of small volumes was found by the present inventors to result in extremely low OMV recovery as determined by BCA protein assay (results not shown). Thus, the invention also provides a method of sterilising an OMV preparation, wherein a stable OMV preparation (prepared according to any embodiment of the invention) is filtered through at least one filter membrane having a pore size of about 0.2 microns.

The stable preparations of the invention are particularly suitable for use in the filtration/sterilisation methods described above, and allow high recovery of OMVs as measured by post-filtration % protein recovery. The pre-filtration OMV preparations are substantially monodisperse, with the majority of their constituent particles having a diameter smaller than the pore size of the filter membranes. This prevents the filter from becoming blocked by binding of the particles to the membrane, and ensures that a high proportion of the OMVs are recovered. This high % recovery is a significant advantage, especially when filtration processes are scaled up for manufacture.

The filtration/sterilisation methods of the invention allow for superior recovery of OMVs, as shown in Table 3.

The invention also provides stabilised preparations of OMVs.

In one embodiment of the invention, OMV preparations are provided that comprise OMVs having a sufficiently positive or negative surface charge to substantially prevent aggregation.

In another embodiment, OMV preparations are provided comprising OMVs suspended in a solution, wherein the zeta potential of the solution is sufficiently positive or negative to substantially prevent aggregation. Preferably, the zeta potential is outside the range −15 mV to 15 mV, more preferably outside the range −30 mV to 30 mV, most preferably outside the range −40 to 40 mV.

In yet another embodiment, OMV preparations are provided comprising OMVs in a solution having a pH of 8 or above, preferably pH 8.5 or above.

The stability of the preparations of the invention can be maintained over a significant period of time e.g., 24 hours, as shown in Table 2. In certain embodiments of the invention, preparations are provided wherein at least 65%, preferably at least 75% or 85%, more preferably up to 100% of the OMVs have a mean diameter of less than 250 nm, preferably less than 200 nm, less than 180 nm, less than 170 nm, or less than 160 nm, and wherein the preparation remains stable for at least 24 hours.

The OMV preparations of the invention may also comprise wild-type OMVs having a sufficiently positive or negative surface charge to substantially prevent aggregation. Where the preparations comprise wild-type OMVs suspended in a solution, the zeta potential of the solution is preferably outside the range −15 mV to 15 mV, more preferably outside the range −30 mV to 30 mV, most preferably outside the range −40 to 40 mV.

In another aspect of the invention, the OMV preparations may comprise OMVs suspended in a buffer, wherein the buffer has a sufficiently positive or negative zeta potential to substantially prevent aggregation.

Sterile OMV preparations are particularly useful in the production of pharmaceutical products, eg vaccines, and thus the invention also comprises OMVs suspended in a solution, wherein the solution has a sufficiently positive or negative zeta potential to substantially prevent aggregation, and wherein the OMVs have been filtered through at least one filter membrane having a pore size of 0.2 microns or less. The filtration of the OMVs through a filter having a pore size of 0.2 microns or less renders the preparation sterile. Preferred filters are those having an average pore diameter of 0.2 µm.

The OMVs of the preparations of the invention are preferably not those from the known vaccine (Claassen et al, 1996), and hence it is preferred that the OMVs are not genetically modified so as to delete PorB and/or express more than one PorA protein. Specifically, it is preferred that the OMVs are not genetically modified to express more than one of the following PorA subtypes:—

P1.7-2,4
P1.12,13
P1.5-2,10.

OMV preparations containing particular antigens are known for use as effective vaccines. The stable preparations of the invention are ideally suited to such use, and thus the invention further provides for the use of an OMV preparation according to any embodiment of the invention in the preparation of a vaccine.

The stable preparations of the invention are particularly suitable for use as intranasal vaccines. Specifically, a suspension of stable OMVs will disperse evenly in a mist dispenser, and smaller particles are preferentially taken up by the nasal associated lymphoid tissue. Stable OMV preparations of the invention can also be used as adjuvants in vaccines administered via the intranasal route. Thus the present invention provides methods of medical treatment or methods of prevention of disease (e.g., by vaccination) such as disease caused by one of the microorganisms mentioned earlier (e.g., Neisserial disorders and the other disorders mentioned above) using preparations of OMVs as described herein. In addition, the invention provides the OMV preparations described herein for use in medical treatment, and the use of the OMVs described herein in the manufacture of a medicament for the treatment or prevention of a medical disorder as described herein. Preferably such methods, uses and medicaments are for intranasal administration, e.g., vaccines for intranasal administration.

Also provided by the invention is the use of a substance that is capable of adjusting zeta potential in the manufacture of a medicament for treating or preventing meningococcal disease. The invention also provides the use of the buffers and solutions described herein (e.g., buffers or solutions having the capability of increasing the magnitude of the surface charge of OMVs) in the inhibition of aggregation of OMVs and/or the stabilisation of OMVs. The invention also provides the use of buffers or solutions having a high pH (as defined herein) in the inhibition of aggregation of OMVs and/or the stabilisation of OMVs.

In a specific embodiment of the invention described in more detail below, the invention includes providing a buffer system that maintains a high surface charge (measured as zeta potential) on the OMVs, resuspending the OMVs in a buffer that maintains a high positive or negative zeta potential, homogenising the OMVs in this buffer to ensure any aggregates are separated and filtering the homogenate through a 0.2 µm filter that has been pre-wetted with this buffer. A particularly effective set of conditions for filtration of *Neisseria*

OMVs is in an 0.2M glycine pH 8.0, 3% sucrose buffer. The OMVs are homogenised in this buffer to disrupt any aggregates. The filter is pre-wetted with the buffer and the OMVs are then passed through the filter with very low loss caused by binding to the filter.

The invention is now further illustrated in the following examples, together with the accompanying drawings and tables, in which:—

Table 1 shows the effect of pH and ionic concentration on OMV aggregation;

Table 2 shows the stability of OMV preparations of the invention over a 24 h period following homogenisation;

Table 3 shows the protein recovery following filtration of the OMV preparations

Table 4 shows the zeta potentials of OMV preparations in buffers of pH 8-10.

Table 5 shows the mean particle size and zeta potential of OMVs after storage.

Table 6 shows a summary of filter studies on the OMVs.

EXAMPLE 1

Stabilisation and Sterilisation of OMVs

A: Effect of pH and Ionic Strength on Aggregation of OMVs
Deoxycholate-extracted outer membrane vesicles (DOMVs) were isolated from cultures of *Neisseria lactamica* according to the method described by Frasch et al. (2001). The isolated OMVs were then suspended in either 0.1M citric acid —$Na_2HPO_4$, pH4 buffer or 0.2M glycine-NaOH pH9 buffer in order to determine the effect of pH on OMV aggregation. Some of these buffered OMV suspensions were also incubated in the presence of 0.1M $CaCl_2$ to determine the effect of ionic strength on OMV aggregation.

After incubation, samples were examined by light microscopy and scored for aggregation. Samples were also analysed using a Zetasizer (Malvern Instruments) and results are presented in Table 1. OMVs suspended in water for injection were found to be highly aggregated, with zeta potentials in the range −10 to 10 mV (results not shown). However, a combination of high pH and absence of $CaCl_2$ gave higher values for zeta potential and low or no aggregation was observed.

Figure 1:
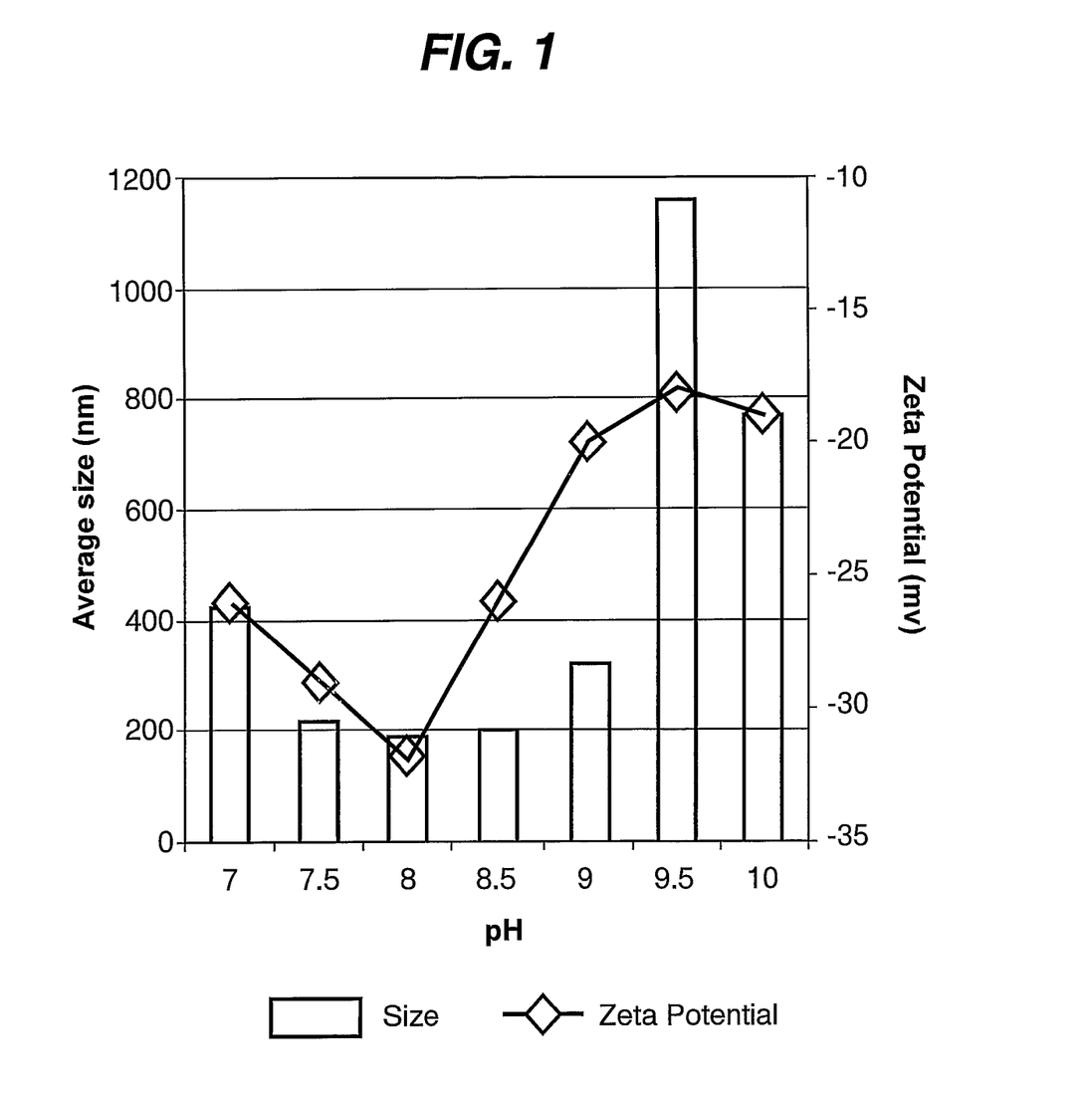
FIG. 1 shows the correlation between average particle size and zeta potential.

Next, the average particle size and zeta potential of *N. lactamica* OMVs resuspended in 0.2M glycine at pH values ranging from 7 to 10 were measured an the results are shown in FIG. 1. The lowest average particle size corresponds with the greatest negative zeta potential. Small particle sizes can be achieved by further increases in the magnitude of the negative zeta potential.

B: Effect of Buffer Composition on Aggregation of OMVs
Next, the following buffers were assessed for their effect on the aggregation of OMV suspensions:
0.2M Glycine-NaOH buffer solution pH8.0
0.2M Glycine-NaOH buffer solution pH9.0
0.2M Glycine-NaOH buffer solution pH10.0

OMVs in water for injection (WFI)+3% (w/v) sucrose were diluted in the buffer solutions above to a concentration of 300 μg/ml and left to equilibrate overnight at 4° C. The OMV solutions were then analysed using the Zetasizer (Malvern Instruments). All 0.2M glycine buffers resulted in OMVs with low aggregation.

C: Comparison of Buffers with Water for Injection
Water for injection and 0.2M glycine buffers with a pH range of 8-10 were tested. OMVs were diluted to a concentration of 250 μg/ml in the appropriate buffer and after equilibration at 4° C. they were sized and the zeta potential measured. The zeta potentials for the buffers are shown in Table 4. The glycine buffers at pHs 8-10 all resulted in OMVs with lower aggregation compared to OMVs suspended in water for injection.

D: Post Homogenisation Size Distribution of Stabilised OMVs
A two-step homogenisation using an Ultra-turrax T25 homogeniser was tested to determine the effect of homogenisation speed on the aggregation and stability of the OMVs in 0.2M glycine pH 9.0 buffer at a concentration of 300 μg $ml^{-1}$.

After 5 min on ice at 8000 rpm, three peaks were observed. However, after a further homogenisation at 9500 rpm for 5 min on ice, and equilibration for 10 minutes, one major peak was observed at approximately 170 nm.

The OMVs were resized after 30 min, 5 h and 24 h (Table 2). As shown in Table 2, the size distribution of the OMVs remained substantially stable over 24 hours.

From this experiment, a two-step homogenisation (8000 rpm/5 min followed by 9500 rpm/5 min at 4° C.) achieved a stable preparation of OMVs. These results were confirmed using OMVs suspended in 0.2M glycine buffer pH8 3% sucrose.

E: Filtration and Sterilisation of Stabilised OMV Preparations
Our initial studies of 0.2 μm filtration of OMV suspensions in buffers that do not provide stabilising conditions (i.e., those in which the OMVs are aggregated) showed no recovery in the post filtration samples.

The filtration of stabilised OMV preparations was assessed using Mini KleenPak EKV filter capsules (average pore diameter 0.65/0.2 μm), Pall UK Ltd.

The filters were tested with 6×150 ml batches of *N. lactamica* OMVs prepared in 0.2 mM glycine pH 8.0 3% sucrose. These OMV suspensions were each passed through 2 filters and samples taken before and after each filter. Passage through two 0.2 μm filters is an accepted method of sterilisation for a pharmaceutical product. The pre and post filtration protein concentrations are shown in Table 6. It can be seen that greatest loss in protein concentration is seen with the first filter and there is little loss on passage through the second filter. The range of protein recoveries was 31-54% with a mean recovery of 39.7%.

Figure 2:
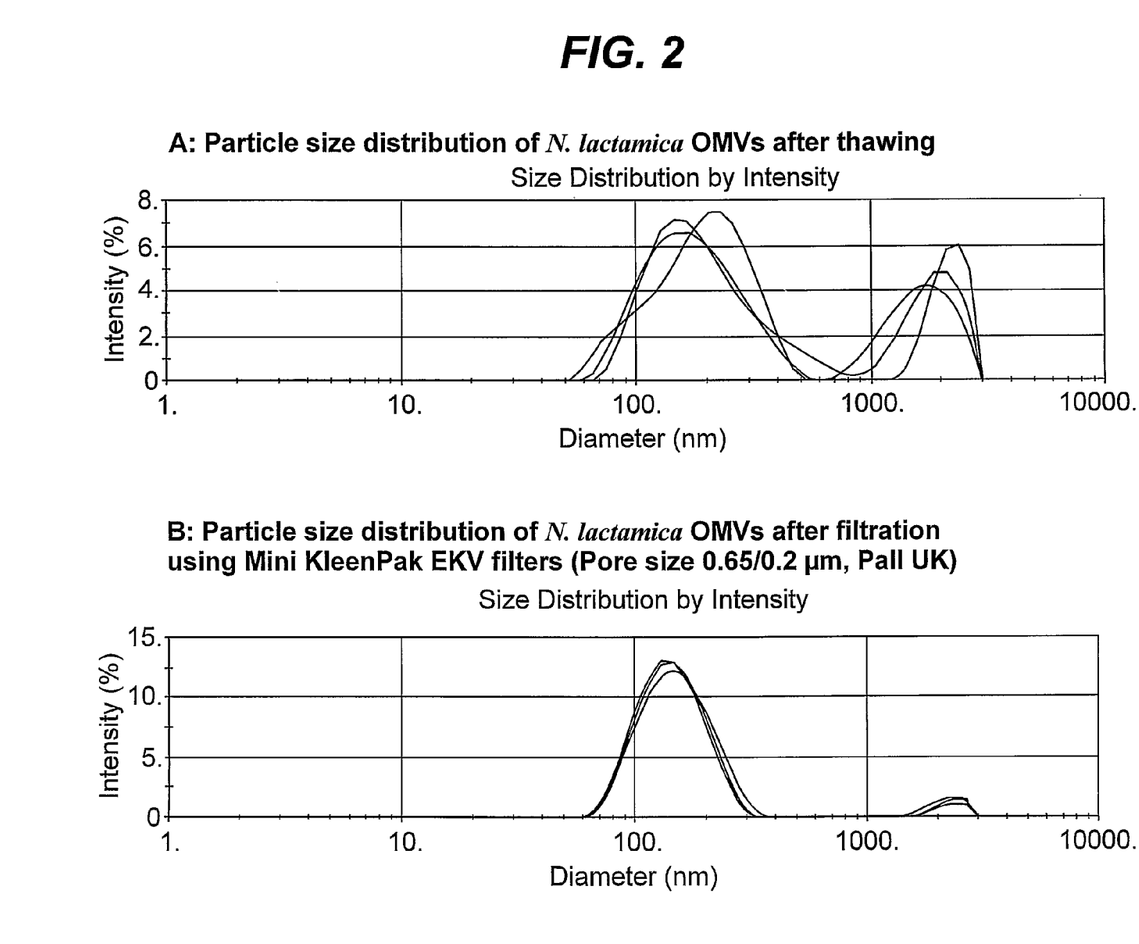
FIG. 2 shows the effect of filtration on OMV size. The particle size distribution is shown before filtration (A) and post filtration (B) (B).

The particle size profile (determined with a Malvern Instruments Zetasizer Nano ZS) for OMVs stored frozen at −20° C. for 1 week and then thawed is shown in FIG. 2A. FIG. 2B shows the same batch of OMVs after filtration through the Mini KleenPak EKV filter capsules. It can be seen that there is a greatly reduced proportion of large size OMVs in the sample. The three lines on each graph represent three determinations on the same sample.

In a further experiment, the filtration of stabilised OMV preparations was assessed using a number of different filter types:—
0.8 μm prefilter/0.2 μm filter polyethersulfone (PES) membrane (Pall Filtration)
0.2 μm PVDF membrane (Pall)

0.45 µm PVDF membrane (Pall)
0.2 µm Fluorodyne (Pall)
0.2 µm Minisart™ (Sartorius)
0.8 µm prefilter/0.65 µm Sartoclean™ (Sartorius)
0.65 µm prefilter/0.45 µm Sartobran™ (Sartorius)
0.45 µm prefilter/0.2 µm filter Sartobran™ cellulose nitrate membrane (Sartorius)

The filters were tested as either syringe filters or 47 mm discs contained in a filter housing and attached to a peristaltic pump to control the flow rate at 4 ml min$^{-1}$.

The protein recoveries obtained with a range of buffers and filters are shown in Table 3. When the OMVs were resuspended in water for injection with 3% sucrose, poor recoveries were obtained and the filters quickly blocked. The use of 0.2M glycine pH 8.5 allowed recoveries of 28-40% and this was improved by use of the pH 8.0 buffer, where recoveries greater than 75% were obtained with the Sartobran filters. A further improvement in recoveries was observed when 0.2M glycine pH 8.0 3% sucrose was used and the filters were pre-wetted with this buffer. With these conditions it was possible to filter the OMVs through the Sartobran filter with a 97% recovery and then conduct a second filtration on the same OMVs with an 81% recovery.

Figure 3A:
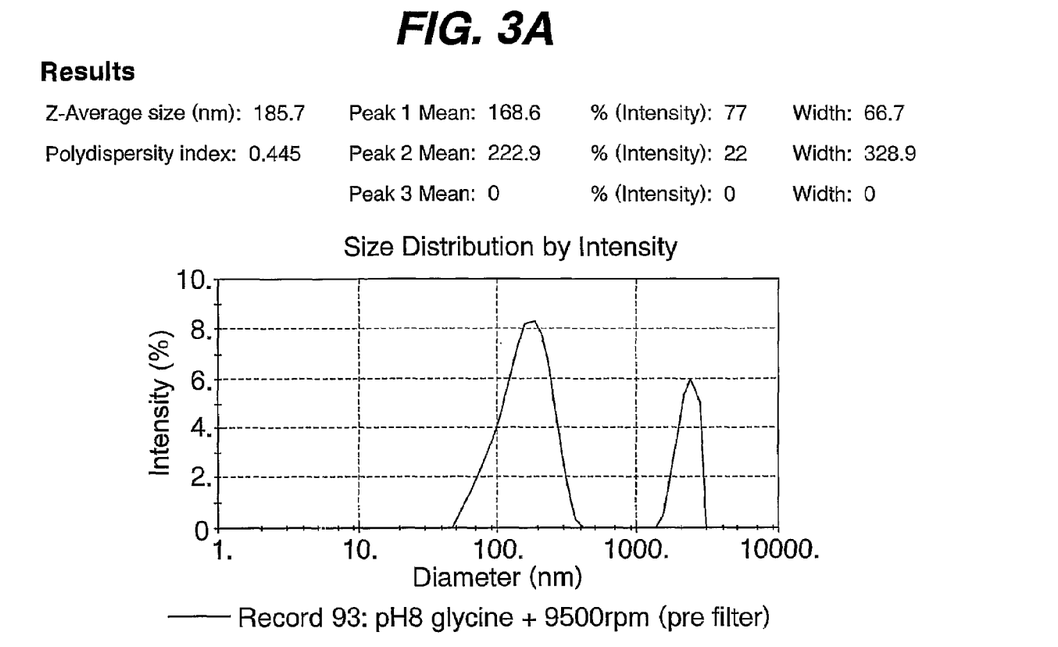
FIG. 3 shows the effect of filtration on OMV size. OMVs are suspended in 0.2M glycine pH 8.0 and the particle size distribution is shown before filtration (A), post 0.8 μm prefilter/0.2 μm filter polyethersulfone (PES) membrane (Pall Filtration) (B), and post 0.45 μm prefilter/0.2 μm filter cellulose nitrate membrane (Sartorius) (C).
Figure 3B:
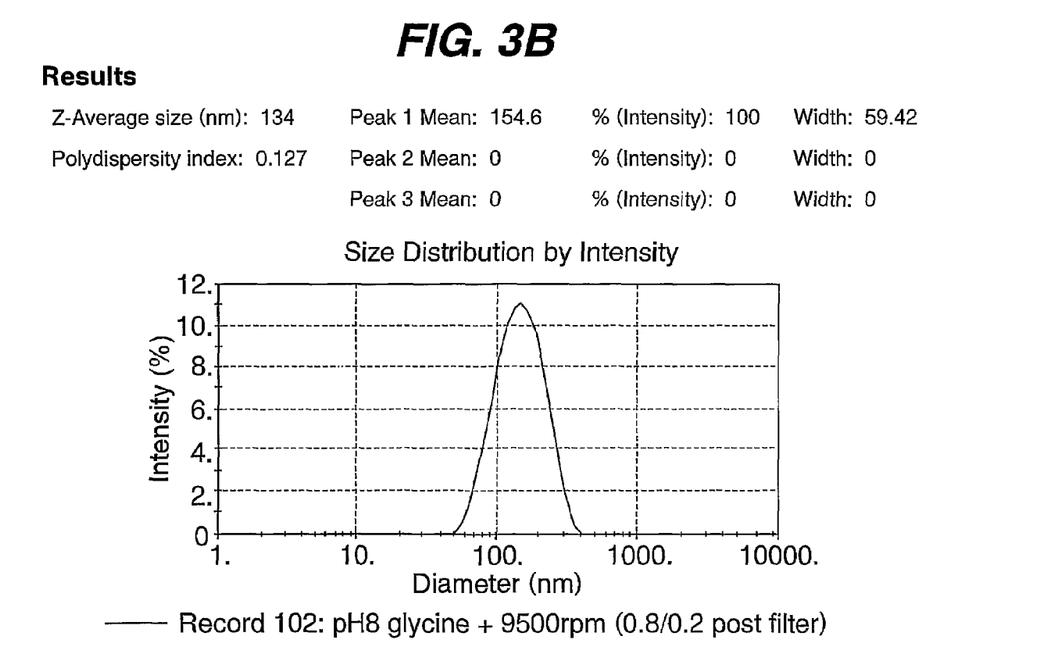
Figure 3C:
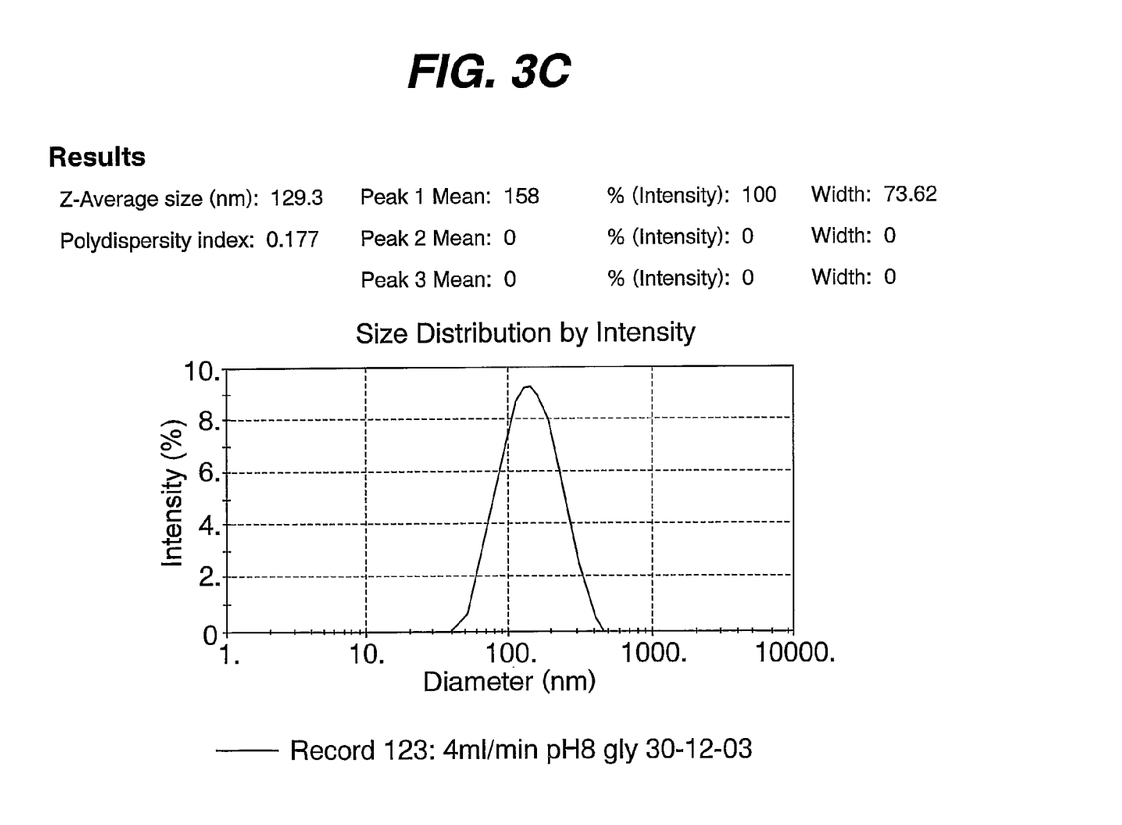

The particle sizing results are shown in FIG. 3 and both the Sartobran™ 0.45 µm/0.2 µm filter and the Pall 0.8 µm/0.2 µm filter types result in a single peak of approximately 154.6 and 158 nm respectively. FIG. 3A is the starting material profile of OMVs at 300 µg/ml$^{-1}$ in 0.2M glycine pH 8 3% sucrose. These OMVs have been homogenised at 8000 rpm followed by 9500 rpm and allowed to equilibrate at 4° C. overnight. FIG. 3B shows the post-filtration profile of OMVs after filtration through the Pall 0.8 µm/0.2 µm membrane and FIG. 3C is the post-filtration profile after filtration through the Sartobran™ cellulose nitrate membrane 0.45 µm/0.2 µm filter. Although these methods gave comparable results, the Pall membrane was more prone to blocking and a greater quantity of OMV material was present on this membrane after filtration compared with the cellulose nitrate membrane.

The invention therefore provides a method for stably maintaining OMVs in suspension as separate vesicles, thus enabling the OMVs to be filtered with low loss.

EXAMPLE F

Particle Size and Zeta Potential of *Neisseria lactamica* after Storage

The particle sizes and zeta potentials of *N. lactamica* (Y92 1009) Outer Membrane Vesicles (OMV) stored in PBS or Glycine/sucrose buffer was measured.

Size analysis of the *N. lactamica* OMVs suspended in phosphate buffered saline shows the presence of large (1000 µm) aggregates and this lead to problems when filter sterilizing the vaccine through a double 0.2 µm filter. Thus, we have explored a range of conditions to ensure that the OMVs remain in suspension as discrete particles.

Particle size and zeta potential measurements were performed as per manufacturers instructions (Malvern Instruments Zetasizer nano series—Nano-ZS and DTS nano Dispersion technology software Version 3.00) using Zetasizer nano Series disposable folded capillary cells (Cat No DTS1060)

Figure 4:
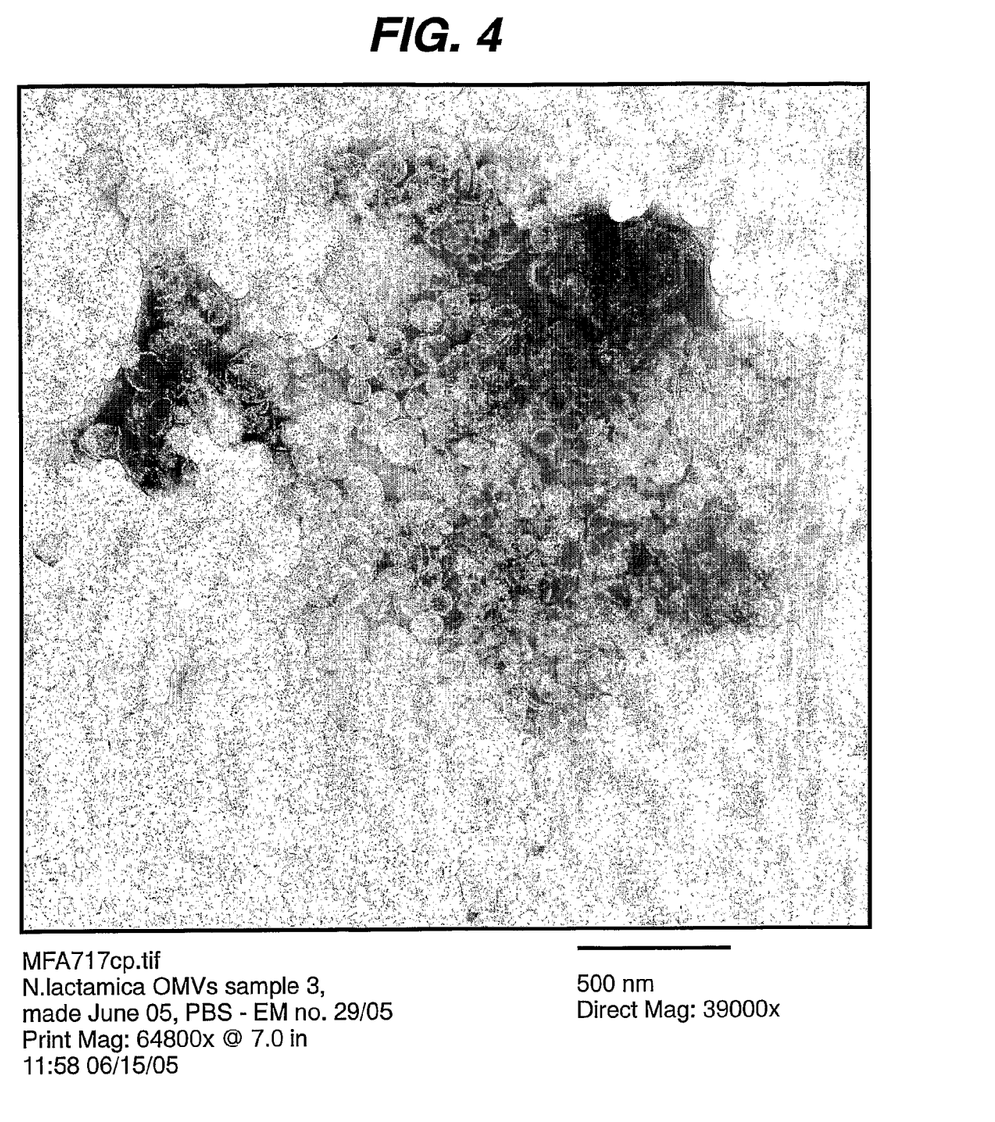
FIG. 4 is an electronmicrograph of OMVs in PBS.
Figure 5:
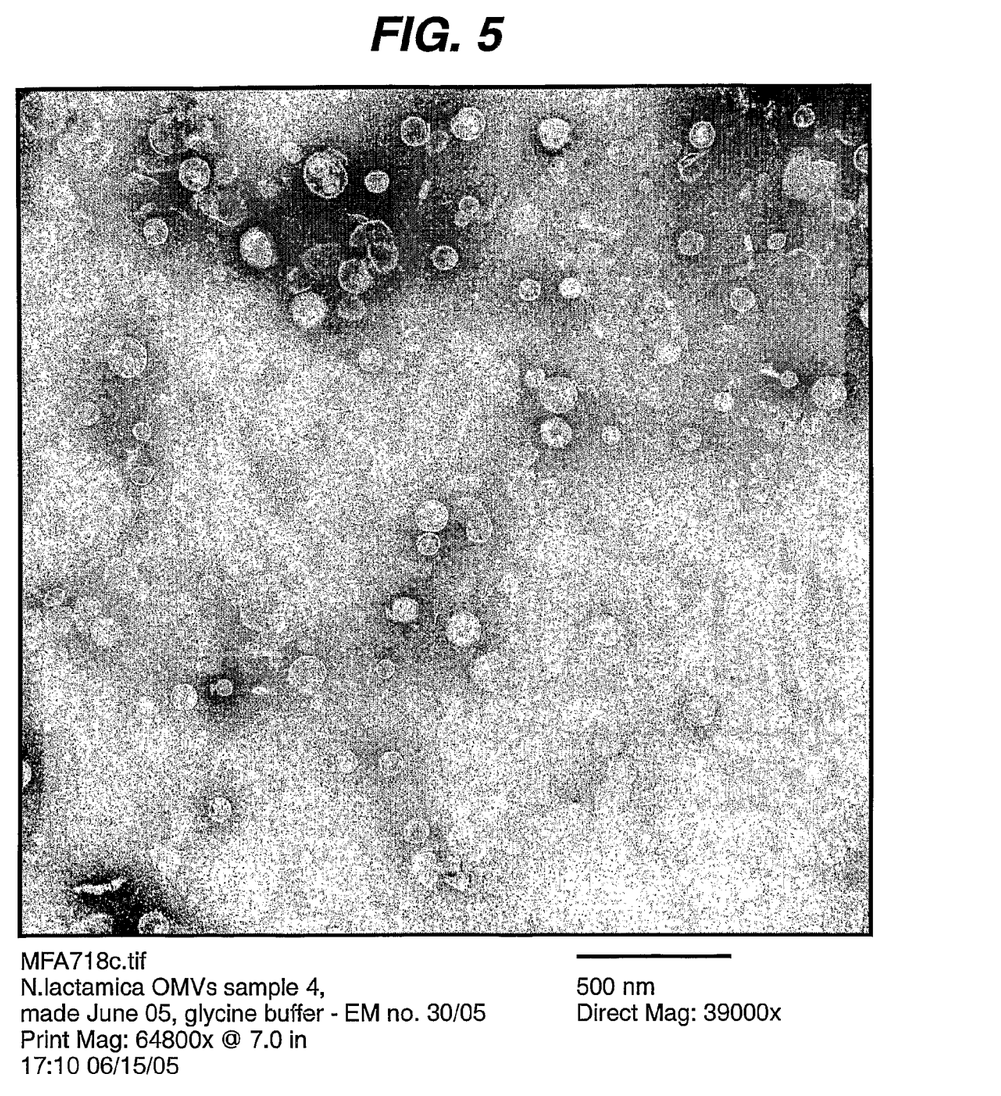
FIG. 5 is an electronmicrograph of a non-aggregating preparation of OMVs according to the invention.

Samples of OMVs frozen on 20.08.04 stored in PBS or 0.2M glycine pH 8.0, 3% sucrose were thawed on 13.06.05 at room temperature, vortexed for 5 minutes and mixed thoroughly using a pipette before testing. The OMVs stored in PBS had a larger particle size than could be measured as they had formed into large aggregates (Table 5). This is confirmed by electron microscopy (FIG. 4). The OMVs stored in 0.2M glycine pH 8.0, 3% sucrose at –20° C. for 10 months showed a low particle size (Table 5) and discrete vesicles were seen by electron microscopy (FIG. 5). FIG. 4 shows OMVs suspended in PBS, which are highly aggregated.

Freshly made samples of OMVs resuspended in either PBS or 0.2M glycine pH 8.0, 3% sucrose were homogenized at 11,000 rpm for 5 minutes and then allowed to stand at room temperature for 5 minutes before testing. The particle size data was essentially the same as that for OMV stored frozen for 10 months. The OMVs in PBS were aggregated whilst those in 0.2M glycine pH 8.0, 3% sucrose remained as predominantly discrete OMVs.

REFERENCES

Arigita C, Jiskoot W, Westdijk J, van Ingen C, Hennink W E, Crommelin D J, Kersten G F (2004). Stability of mono- and trivalent meningococcal outer membrane vesicle vaccines. Vaccine 22: 629-42.

Fredriksen J H, Rosenqvist E, Wedege E, Bryn K, Bjune G, Froholm L O, Lindbak A K, Mogster B, Namork E, Rye U, et al. (1991). Production, characterization and control of MenB-vaccine "Folkehelsa": an outer membrane vesicle vaccine against group B meningococcal disease. NIPH Ann. 14: 67-79

Sierra G V, Campa H C, Varcacel N M, Garcia I L, Izquierdo P L, Sotolongo P F, Casanueva G V, Rico C O, Rodriguez C R, Terry M H. (1991) Vaccine against group B *Neisseria meningitidis*: protection trial and mass vaccination results in Cuba. NIPH Ann. 14:195-207.

Claassen I, Meylis J, van der Ley P, Peeters C, Brons H, Robert J, Borsboom D, van der Ark A, van Straaten I, Roholl P, Kuipers B, Poolman J. (1996) Production, characterization and control of a *Neisseria meningitidis* hexavalent class 1 outer membrane protein containing vesicle vaccine. Vaccine. 14: 1001-8.

Frasch C E, van Alphen L, Hoist J, Poolman J T and Rosenqvist E. (2001). Outer membrane protein vesicle vaccines for meningococcal disease. From: Methods in Molecular Medicine vol 66: Meningococcal Vaccines: Methods and Protocols. Edited by A J Pollard and M C J Maiden. Humana Press, Totawa N.J. Pages 81-107.

TABLE 1

Aggregation, mean particle size and zeta potential of *N. lactamica* OMVs.
Mean of 4 determinations.
pH 4.0 buffer: 0.1M citric acid, Na$_2$HPO$_4$
pH9.0 buffer: 0.2M glycine, NaOH

| pH | 0.01M CaCl$_2$ | Aggregation score (determined by light microscopy*) | Mean diameter (nm) & standard deviation | Mean zeta potential (mV) & standard deviation |
|---|---|---|---|---|
| 4 | Yes | +++ | 19975 (8833) | 5.9725 (0.20) |
| 4 | No | +++ | 17775 (1627) | 4.95 (1.77) |
| 9 | Yes | +++ | 17300 (7778) | −5.76 (0.27) |
| 9 | No | + | 364.6 (146) | −40.75 (11.05) |

*Aggregation score +++ very aggregated, + weakly aggregated

TABLE 2

Stability of OMV Preparations
OMVs suspended in pH 9 glycine buffer, homogenised at 8000 rpm
for 5 mins, followed by 9500 rpm for 5 mins, equilibrated and sized.

| Equilibration Time | Mean diameter of particles in major peak | % (intensity) |
|---|---|---|
| 10 mins | 149.1 | 76 |
| 30 mins | 151.5 | 72 |
| 5 h | 154.6 | 68 |
| 24 h | 137.5 | 75 |

TABLE 3

Filtration of *N. lactamica* OMVs

| Buffer | Filter | Start Conc (μg/ml) | Post filter conc (μg/ml) | % Recovery |
|---|---|---|---|---|
| Water for injection 3% sucrose | Pall polyethersulphone 0.8/0.2 μm | 231 | 21 (1st 2 ml) 0 (2-4 ml) | 9% (1st 2 ml) 0% (2-4 ml) |
| Water for injection 3% sucrose | Pall PVDF 0.2 μm | 231 | 91 (1st 2 ml) 0 (2-4 ml) | 39% (1st 2 ml) 0% (2-4 ml) |
| Water for injection 3% sucrose | Pall PVDF 0.45 μm | 231 | 57 (1st 2 ml) 20 (2-4 ml) | 57 (1st 2 ml) 9% (2-4 ml) |
| 0.2M Glycine pH 8.5 | Sartorius Minisart 0.2 μm | 225 | 89 | 40% |
| 0.2M Glycine pH 8.5 | Pall Fluorodyne 2 0.2 μm | 225 | 74 | 33% |
| 0.2M Glycine pH 8.5 | Pall Super 0.8/0.2 μm | 225 | 64 | 28% |
| 0.2M Glycine pH 8.0 | Sartorius Sartoclean 0.8/0.65 μm | 306 | 153 | 50% |
| 0.2M Glycine pH 8.0 | Sartorius Sartobran 0.45/0.2 μm | 306 | 235 | 77% |
| 0.2M Glycine pH 8.0 | Sartorius Sartobran 0.65/0.45 μm | 306 | 243 | 79% |
| 0.2M Glycine pH 8.0 3% sucrose | Pall polyethersulphone 0.8/0.2 μm (pre-wetted) | 548 | 382 | 70% |
| 0.2M Glycine pH 8.0 3% sucrose | Sartorius 0.45/0.2 μm cellulose nitrate Sartobran (pre-wetted) | 310 | 300 | 97% |
| 0.2M Glycine pH 8.0 3% sucrose | Sartorius 0.45/0.2 μm cellulose nitrate Sartobran (pre-wetted) | 254 (2nd filtration) | 206 | 81% |

TABLE 4

Buffer Zeta Potentials

| Buffer/pH | zeta potential (mV) |
|---|---|
| 0.2M glycine buffer - pH 8.0 | −32.8 |
| 0.2M glycine buffer - pH 9.0 | −20.76 |
| 0.2M glycine buffer - pH 10.0 | −20.45 |

TABLE 5 mean particle size and zeta potential of *N. lactamica* OMVs.

| Sample | Mean ± SD Mean particle size (nm) | Zeta Potential (mV) |
|---|---|---|
| OMVs stored at −20° C. in PBS for 10 months and thawed | >1000 | 0.01 ± 2.4 |
| OMVs stored at −20° C. in 0.2M glycine pH 8.0, 3% sucrose for 10 months and thawed | 159.1 ± 0.2.66 | −25.88 ± 4.57 |
| Freshly prepared OMVs resuspended in PBS | >1000 | −0.01 ± 0.034 |
| Freshly prepared OMVs resuspended in 0.2M glycine pH 8.0, 3% sucrose | 149.4 ± 0.219 | −24.3 ± 4.195 |

TABLE 6

Summary of filter studies using Mini KleenPak EKV filters
(Pore size 0.65/0.2 μm, Pall UK Order number KA02EKVP2S), all
material had been stored at −20° C. for 1 week and thawed at 4° C.
overnight before use.

| | | Lowry Protein (ug/ml) | | | Size | |
|---|---|---|---|---|---|---|
| | | Pre | Post | % recovery | Pre | Post |
| Batch 1 | 1 | 386 | 176 | | 230.73 | 144.76 |
| | 2 | 176 | 167 | 43 | 144.76 | 142.06 |

TABLE 6-continued

Summary of filter studies using Mini KleenPak EKV filters
(Pore size 0.65/0.2 μm, Pall UK Order number KA02EKVP2S), all
material had been stored at −20° C. for 1 week and thawed at 4° C.
overnight before use.

| | | Lowry Protein (ug/ml) | | | Size | |
|---|---|---|---|---|---|---|
| | | Pre | Post | % recovery | Pre | Post |
| Batch 2 | 1 | 409 | 141 | | 270.26 | 166 |
| | 2 | 141 | 129 | 31 | 166 | 153.83 |
| Batch 3 | 1 | 377 | 175 | | 220.55 | 173.96 |
| | 2 | 175 | 147 | 38 | 173.96 | 189 |
| Batch 4 | 1 | 363 | 150 | | 219.66 | 167.44 |
| | 2 | 150 | 163 (150) | 41 | 167.44 | 182.7 |
| Batch 5 | 1 | 420 | 182 | | 214 | 151 |
| | 2 | 182 | 129 | 31 | 151 | 180 |
| Batch 6 | 1 | 372 | 191 | | 177 | 147 |
| | 2 | 191 | 200 | 54 | 147 | 151 |

The invention claimed is:
1. A method of preventing aggregation of outer membrane vesicles (OMVs) comprising:
(i) obtaining a preparation of OMVs in a solution,
(ii) measuring the aggregation of the OMVs in said solution,
(iii) if the OMVs are aggregated, adjusting zeta potential of the OMVs in the solution, and returning to step (ii).

2. A method according to claim 1, wherein the OMVs are aggregated when they have a mean diameter in excess of 200 nm.

3. A method according to claim 1, wherein the zeta potential is adjusted by altering pH of the solution.

4. A method according to claim 1, wherein the zeta potential is adjusted by altering the ionic strength of the solution.

5. A method according to claim 1, further comprising a homogenisation step after step (iii).

6. A method according to claim 1, wherein the preparation of OMVs is subsequently frozen.

7. A method according to claim 1, wherein magnitude of the zeta potential is adjusted to be more negative than the starting value by −5 mV to −30 mV, −10 mV to −20 mV, −5 mV to −15 mV, −8 mV to −12 mV, or −10 mV.

8. A method according to claim 1, wherein the solution is a buffer solution.

9. A method according to claim 1, comprising adjusting the zeta potential of the OMVs in the solution to fall outside the range −15 mV to 15 mV.

10. A method according to claim 3, wherein the pH is altered to be equal to or greater than pH 8.

11. A method according to claim 3, wherein the pH is altered to be equal to or less than pH 6.

12. A method according to claim 4, wherein the ionic strength of the solution is altered by the addition of ions to the solution.

13. A method according to claim 1, wherein the zeta potential is adjusted by altering temperature of the solution.

14. A method according to claim 13, wherein the zeta potential is adjusted by lowering the temperature of the solution.

15. A method of according to claim 1, wherein the preparation is subsequently filtered through a filter membrane.

16. A method according to claim 15, further comprising a homogenisation step prior to the filtering step.

17. A method according to claim 15, wherein, subsequent to filtering through the filtering membrane, at least 90% of the OMVs have a mean diameter of less than 200 nanometres.

18. A method according to claim 15, wherein, subsequent to filtering through the filtering membrane, at least 90% of the OMVs have a mean diameter of less than 180 nanometres.

19. A method according to claim 15, wherein, subsequent to filtering through the filing filtering membrane, at least 90% of the OMVs have a mean diameter of less than 160 nanometres.

20. A method according to claim 15, wherein the filter membrane has a pore size of from 0.2-2 microns.

21. A method according to claim 15 for sterilizing an OMV preparation, wherein the filter membrane has a pore size of about 0.2 microns.

* * * * *

UNITED STATES PATENT AND TRADEMARK OFFICE
CERTIFICATE OF CORRECTION

| | | |
|---|---|---|
| PATENT NO. | : 7,820,185 B2 | Page 1 of 1 |
| APPLICATION NO. | : 11/632794 | |
| DATED | : October 26, 2010 | |
| INVENTOR(S) | : Gorringe et al. | |

It is certified that error appears in the above-identified patent and that said Letters Patent is hereby corrected as shown below:

In the claims:

Column 16, line 11, in claim 17, "the filtering membrane" should read:

--the filter membrane--;

Column 16, line 14, in claim 18, "the filtering membrane" should read:

--the filter membrane--; and

Column 16, line 17, in claim 19, "the filing filtering membrane" should read:

--the filter membrane--;

Signed and Sealed this
Fourteenth Day of May, 2013

Teresa Stanek Rea
*Acting Director of the United States Patent and Trademark Office*